United States Patent [19]

Davis

[11] 4,100,411
[45] Jul. 11, 1978

[54] BIASING ARRANGEMENT FOR A CORONA DISCHARGE DEVICE

[75] Inventor: Thomas G. Davis, Pittsford, N.Y.

[73] Assignee: Xerox Corporation, Stamford, Conn.

[21] Appl. No.: 790,725

[22] Filed: Apr. 25, 1977

Related U.S. Application Data

[63] Continuation of Ser. No. 541,545, Jan. 16, 1975, abandoned.

[51] Int. Cl.² ............................................. G03G 15/00
[52] U.S. Cl. .................................. 250/324; 250/326
[58] Field of Search ........................ 250/324, 325, 326

[56] References Cited

U.S. PATENT DOCUMENTS

| | | | |
|---|---|---|---|
| 3,813,547 | 5/1974 | Silverberg | 250/324 |
| 3,961,193 | 6/1976 | Hudson | 250/324 |

Primary Examiner—Craig E. Church

[57] ABSTRACT

A biasing arrangement for a corona discharge device including a conductive shield partially surrounding a corona electrode comprising means for applying a first high D.C. potential to the wire and a second high D.C. potential to the shield, the potential difference between the wire and the shield being sufficiently small to substantially inhibit corona current. A high voltage pulse train is superimposed on the shield which periodically increases the potential difference between the wire and the shield to foster ion generation adjacent the wire. Between pulses, the shield is returned to the second potential to again inhibit further ion generation while concurrently permitting ion movement toward a surface to be charged rather than toward the shield itself. Pulse duration and repetition rate are selected to enhance the efficiency of the corona device.

14 Claims, 2 Drawing Figures

BIASING ARRANGEMENT FOR A CORONA DISCHARGE DEVICE

This is a continuation of application Ser. No. 541,545, filed Jan. 16, 1975 now abandoned.

BACKGROUND OF THE INVENTION

This invention relates to methods and apparatus for electrostatically charging a surface and more particularly to improved corona generating methods and apparatus therefore usable in electrostatic recording and reproducing equipment or in any other application where it is desirable to efficiently charge a selected medium.

In electrostatic recording and reproducing processes such as the electrophotographic process known as xerography, it is necessary to sensitize a photoreceptor structure by charging at least one surface thereof to a potential which is preferably uniform. Subsequent to or simultaneously with the sensitizing of the photoreceptive strucutre in such electrophotographic processes, the photoreceptor structure is exposed so that a photosensitive layer therein is rendered selectively conductive whereupon a latent electrostatic image is formed which may be then developed using conventional electrophotographic techniques. The developed image is then transferred onto a copy substrate on which it is rendered permanent by means of a fixing process.

In the above-noted electrophotographic process, electrostatic charging techniques are generally relied upon to accomplish such necessary processing steps as the transfer of an electrostatically formed image from a reusable photoreceptor structure to a transfer member and/or tacking and stripping operations associated with such transfer member. While many forms of acceptable techniques for electrostatically charging a surface are known, corona discharge techniques have generally been preferred in applications such as those mentioned above because such techniques are particularly well suited to applying an electrostatic charge to a moving surface and the use of corona discharge techniques allows a selected surface to be rapidly charged to a relatively high potential. Furthermore, since corona generating apparatus generally employ a wire-like electrode, they are advantageous because the charging process involved acts to impose a potential level on the surface being charged which tends to be more uniform than that obtained from other surface charging techniques. Conventional forms of corona generating apparatus are illustrated in U.S. Pat. Nos. 2,836,725 and 2,879,395 and generally comprise one or more wire-like electrodes, known at coronodes, horizontally disposed above the surface to be charged and a shield which may take a plurality of different structural forms, partially disposed about the coronode. In one conventional mode of operation, a high voltage D.C. power supply is connected to the coronode with the requisite polarity for the charging operation which is desired, while a conductive layer associated with the surface to be charged is grounded as are the other terminals of the power supply and the shield. Conventional corona generating apparatus, when used according to the foregoing mode of operation are notoriously inefficient devices in that only a small percentage of the corona current produced at the coronode is delivered to the surface to be charged while a relatively large percentage of the corona current is diverted to the shield and is thereby wasted from the standpoint of applying an electrostatic charge to the surface to be charged.

In an alternate mode of conventional corona generating apparatus operation, a D.C. power supply is connected to the coronode and a conductive layer associated with the surface to be charged while the shield is left unconnected or electrically open. This alternative mode of operation is highly efficient from the standpoint of the current delivered because no current may be diverted by the shield. However, it is much less efficient from the power utilization standpoint because the voltage which is required to be applied to the coronode is much larger than in previously mentioned corona generating apparatus configurations and hence the power supply relied upon must be physically large and capable of producing very large potential levels.

Another arrangement for biasing a corona discharge device in a xerographic machine is taught in U.S. Pat. No. 2,686,989, wherein the corona wire is biased to a high positive corona generating potential, the conductive substrate on which the photoconductive material is held is maintained at ground potential, and the shield is biased to a potential intermediate the corona wire potential and ground. This method also suffers from the disadvantage of a high current to the shield.

The conclusion to be drawn from prior experience with the above different biasing arrangements is that while grounding the shield (or biasing it to various intermediate potentials) promotes corona current at relatively low coronode potential, maintenance of such constant potentials at the shield reduces the efficiency of the corona device by attracting a large percentage of current to the shield.

OBJECTS AND SUMMARY OF THE INVENTION

It would, therefore, be desirable to obtain the high corona current at relatively low corona threshold potentials provided by the grounded shield arrangement while avoiding the decreased efficiency inherent in such devices.

The invention is directed to a novel biasing technique for a corona discharge device which is more efficient than the previous techniques by permitting a high percentage of the corona current generated at the corona wire to be delivered to the surface to be charged.

This invention operates by separating the charging function into two separate time periods during which different functions are performed by the biasing arrangement, a first time during which ion production at the corona wire is promoted, and a second time period in which ion movement toward the surface to be charged is promoted. Alternations between the two periods occur rapidly in a cyclical fashion and the time duration for each period is selected to enhance the overall objective of obtaining a highly efficient, rapidly charging corona device.

The first period during which ion production is promoted is characterized by a high potential difference between the shield and the corona electrode which encourages a large ion production thereat. The second period is characterized by a small potential difference between the coronode and the shield which promotes movement of the ions in the vicinity of the corona electrode toward a surface other than the shield. During both periods the conductive substrate on which the photoconductive material is deposited is held at a constant potential relative to the coronode to promote ion movement thereto, typically group potential.

BRIEF DESCRIPTION OF THE VIEWS

FIG. 1 is an illustrative diagram of a corona discharge device including the biasing arrangement of the invention; and FIG. 2 is a more practical circuit for use with the invention.

DESCRIPTION OF THE PREFERRED EMBODIMENT

Figure 1:
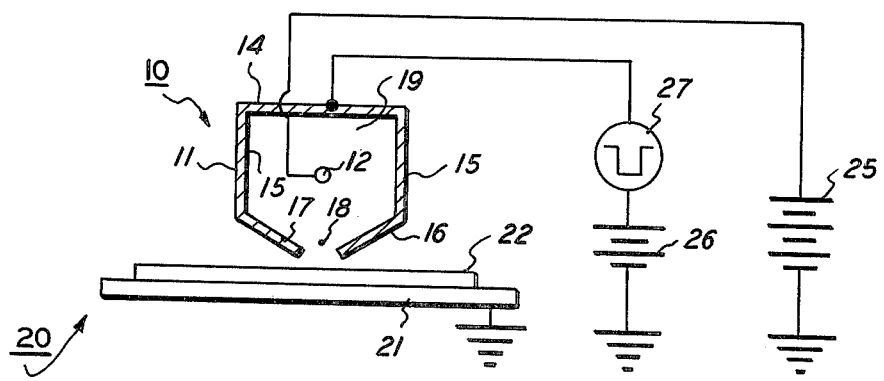

Referring to FIG. 1, there is illustrated a corona discharge device generally designated 10 comprising a conductive shield 11 partially surrounding a corona wire or coronode 12. It should be understood that a plurality of coronodes may be used instead of the one shown in FIG. 1. The shield 11 may, if desired, have an upper or a backing wall 14, side walls 15, and along the bottom or face of the shield, a pair of lips 16 and 17 defining a corona ion slit 18. Desirably, the ion slit extends substantially completely along the length of the electrode across the bottom face and may be fixed or adjustable as desired. The corona wire or coronode 12 is mounted more or less centrally within the shield and electrically insulated from the shield, for example, by insulating end walls 19 and spaced sufficiently from the surfaces of the shield so as to eliminate sparking or electrical avalanche between the wires and the shield.

The shape of the shield described above is one of many acceptable shield configurations known in the xerography art, any of which are usable in the invention and described in detail in U.S. Pat. Nos. 2,879,395 and 2,836,725. The corona discharge device 10 is illustrated as being positioned above and closely adjacent to the surface to be charged such as, for example, a xerographic plate generally designated 20 comprising a conductive support base 21 having on its surface an insulating or photoconductive insulating layer 22. Preferably, the surface 20 is movable relative to the corona discharge device by suitable drive means which may take various forms. One conventional arrangement for moving the photoconductive surface is to construct the surface and support base in the form of a drum with means provided for rotating the drum below the corona discharge device. The motion of the photoconductive surface is generally across the direction of the ion slit 18.

Corona discharge is a breakdown of gas in the region of a very strong electric field such as the electric field at the surface of a conductor having a small radius of curvature. In the case of a given corona discharge device of the type shown in FIG. 1, the strength of the electric field at the coronode is a function of the potential difference between it and adjacent surfaces and the distance to these surfaces. For a given geometry there is a very definite starting potential difference below which essentially no current flows and above which the corona is self-maintaining and the gas surrounding the wire is ionized. Corona current flows by means of these ionized gas molecules or ions and the electrons they release.

In the arrangement of the FIG. 1, the electric field at the wire coronode is affected by the potential difference between the wire and the shield, and the wire and the photoconductive surface. If the potential on the shield is held constant the electric field between it and the wire is also constant during the charging process. In contrast to this, the potential of the photoconductor surface increases during the charging process as charges are deposited thereon, thus reducing the electric field between the photoconductor and the wire. Thus, continuous ion generation is effected to a greater degree by the field between the wire and the shield, which remains relatively strong during the entire charging process. Although ion generation is fostered primarily by a large potential difference between the shield and the wire, it should be noted that this potential difference is limited by the fact that unduly large potentials will cause a spark to bridge these surfaces.

Ions generated by the above process move or migrate from the area adjacent the corona electrode toward adjacent surfaces also as a function of the electric field therebetween. Thus, in prior art biasing arrangements, the same relatively high field between the wire and the shield which produced the ions now causes movement of a substantial majority of these ions to the shield, while a much lesser percentage of the ions flow to the photoconductor surface. Ions delivered to the photoconductor build up a charge on its surface which reduces the electric field between this surface and the wire, further reducing ion flow thereto.

It is for the above noted reasons that conventionally biased corona devices are inefficient, i.e., a large percentage of the corona current is directed to the shield instead of the surface to be charged, the photoconductor.

The invention increases the efficiency of conventional corona charging devices by separating the charging process into separate time intervals. During a first time interval ion generation is promoted, and during a second time interval ion movement to the surface to be charged, instead of the shield, is promoted.

To accomplish this and referring to FIG. 1, the corona wire 12 is attached to a source 25 of high D.C. voltage of a first polarity relative to the substrate 21 on which the photoconductor 22 is carried, which may preferably be grounded.

The shield 15 is biased to a second high D.C. voltage of the same polarity as the coronode from a source 26. The exact value of this voltage may vary depending on the particulars of the corona device such as coronode diameter, spacing, shield configuration, but is chosen to substantially reduce the strength of the electric field at the coronode to below corona the corona onset threshold. While batteries are shown as the sources for the above noted potentials conventional power supplies may be used in a practical environment.

Superimposed on this high D.C. shield bias is a high voltage pulse from a source 27 which serves to increase the field at the coronode 12 and consequently promote ion generation thereat. If the shield and wire were initially biased positive so as to deposit a positive charge on the photoreceptor surface, a negative going pulse is used, as shown in FIG. 1. However, if a negative charge is to be deposited on the photoconductor all polarities would be reversed.

The width or duration of the pulses from source 27 may vary depending upon the specifics of the corona device configuration in order to serve the overall purpose of rapidly generating high ion population without allowing sufficient time for these ions to migrate a substantial distance from the coronode.

The repetition rate for the pulses applied to the shield is selected so that enough time is allowed between pulses to permit a substantial portion of the ions generated during the pulse to move to the photoreceptor surface 22. In a typical arrangement of the type shown in FIG. 1, a pulse width in the range of 2–10 microseconds, and a repetition rate of 200–5000 hertz was found to operate satisfactorily.

Several advantages result from the increased efficiency of the corona discharge device of the invention. First, the corona wire may be operated at a lower potential, thereby decreasing the probability of arcing to the photoreceptor. Secondly, for the same charging current (current arriving at the surface to be charged) the corona current may be reduced by a factor of approximately four over similar prior art arrangements with a consequent reduction in the amount of ozone and growth of compounds on the corona wire, both of which increase with the corona current. Thirdly, since the electric field between the wire and the shield is reduced and a field is produced between the shield and photoreceptor, charged toner, dirt particles, paper fibers, and other air born particles in the vicinity of the corona device are less likely to be deposited on the shield, thereby reducing the probability of malfunction of the corona device over a prolong period of operation.

Figure 2:
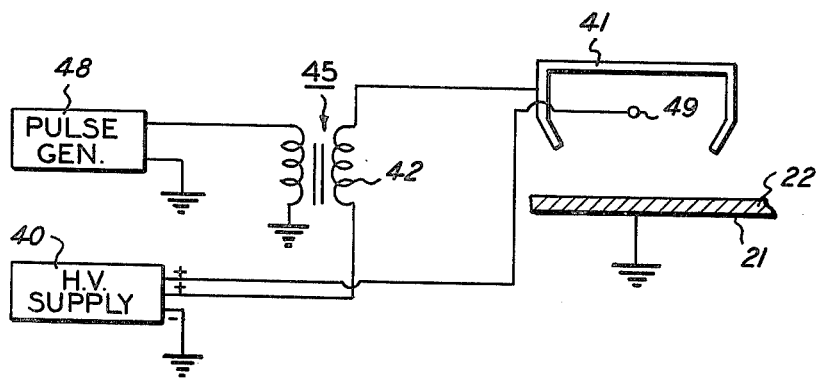

A more practical circuit for coupling the high voltage pulses to the shield is shown in FIG. 2 in which a high voltage D.C. supply 40 is connected to the shield 41 of a corona device through a first winding 42 on a transformer 45. The other transformer winding 46 is connected to a source 48 of negative going high voltage pulses which periodically drives the shield negative with respect to the corona wire 49 (as disclosed above). The corona wire 49 is also coupled in a known manner to a high positive D.C. bias potential. In operation, the shield is continuously biased to a high positive potential but is periodically driven more negative with respect to the shield each time a pulse is generated by the source 49 and coupled to the shield via the transformer 45.

What is claimed is:

1. A corona discharge device comprising
    an elongated corona discharge electrode,
    a conductive shield disposed in partially surrounding relationship with respect to said electrode, said shield being coextensive with said electrode,
    means for applying a high D.C. corona generating potential of a first polarity to said wire,
    means for biasing said shield to a first D.C. potential of said first polarity high enough to substantially extinguish ion formation adjacent said electrode, and
    means for continuously cyclically changing the potential on said shield at a constant rate to a second fixed potential to increase ion production adjacent said electrode and returning said potential to said extinguishing level the duration and frequency of said cyclical changes on said shield operating to direct a substantial majority of said ions under the influence of an electric field to an adjacent surface other than said shield.

2. The combination defined in claim 1 wherein said adjacent surface is a photoconductive surface carried on a conductive substrate, said substrate held at a constant fixed potential for attracting ions to said surface.

3. The combination recited in claim 2 wherein said substrate is held at ground potential.

4. The method of increasing the efficiency of a corona discharge device having an elongated corona electrode partially surrounded by a conductive shield, said device located adjacent a surface to be charged comprising the steps of
    applying a first high voltage D.C. potential to said electrode,
    applying a second D.C. potential to said shield for substantially extinguishing ion production adjacent said wire by decreasing the potential difference between said wire and said shield, and
    superimposing a continuous pulse train at a constant repetitive rate and amplitude on said shield to intermittently promote ion production adjacent said wire by momentarily increasing the potential difference between said wire and said shield, the duration of said pulses being sufficiently short to prevent a substantial majority of said ions from drifting to said shield during said pulse, the time between pulses being sufficiently long to permit a substantial majority of said ions generated during the preceeding pulse to drift to said surface before the occurrence of the succeeding pulse.

5. The method of claim 4 wherein said second potential on said shield is a high positive potential with respect to said adjacent surface but periodically driven negative by said pulse train to cause intermittent ion production prior to being returned to said second potential.

6. A corona discharge device for depositing an electrostatic charge on an adjacent surface comprising
    an corona discharge electrode,
    a conductive shield partially surrounding said electrode,
    means for generating a first electric field between said surface and said electrode, and
    means for generating a second electric field between said electrode and said shield, said second field being continuously alternating between at least two fixed levels at a fixed rate to alternately inhibit ion generation at said electrode and promote ion movement to said surface, and subsequently enhance ion generation at said electrode, the time period during which said second field enhances ion production being sufficiently short to prevent the drift of a majority of said ions to said shield, and the time period during which said second field inhibits ion production being sufficiently long to permit the drift of previously generated ions to said adjacent surface.

7. The combination recited in claim 6 wherein said first electric field is constant.

8. The combination recited in claim 6 wherein said electrode is held at a high constant D.C. potential with respect to said surface.

9. The combination recited in claim 7 further wherein said shield is held at a variable potential with respect to said wire.

10. A corona discharge device for depositing charge on an adjacent surface comprising
    a corona electrode,
    a conductive shield adjacent said electrode,
    means for generating a corona discharge producing electric field intermediate said shield and said electrode, and
    means for periodically varying said field at a continuously fixed repetitive rate and amplitude below the level needed to sustain corona discharge, said latter means operating to alternately promote and inhibit the production of charge, the time during which said production is promoted being sufficiently short to prevent the drift of a majority of said ions to said shield, and the time during which said production is inhibited being sufficiently long to permit the drift of previously generated ions to said adjacent surface.

11. The combination recited in claim 10 wherein said repetitive rate is in the range of 200–500 hertz and the time during which said production is promoted is in the range of 2–10 microseconds.

12. The method of improving the efficiency of a corona charging device for depositing charge on an adjacent surface said device having an elongated electrode adjacent a conductive shield comprising the steps of continuously alternating the electric field between said shield and electrode between first and second fixed conditions and at a fixed rate, said first condtion characterized by the production of ions adjacent said wire, and said second condition characterized by the substantial non-production of ions adjacent said electrode, the duration of said first condition being sufficiently short to prevent the drift of a substantial portion of said ions from said electrode to said shield, the duration of said second period being substantially greater than said first period and long enough to permit the drift of previously generated ions to said adjacent surface.

13. The method of claim 12 wherein said alternating fields are formed by holding said electrode at a substantially constant D.C. potential and changing the potential on said shield.

14. The method of claim 12 wherein the said first condition is accomplished by voltage pulses having a duration in the range of 2–10 microseconds, said pulses occurring at a rate in the range of 200–500 hertz.

* * * * *